(12) United States Patent
Stearns et al.

(10) Patent No.: US 10,174,871 B2
(45) Date of Patent: Jan. 8, 2019

(54) ZERO DEAD VOLUME FITTING ASSEMBLY

(71) Applicant: Valco Instruments Company, L.P., Houston, TX (US)

(72) Inventors: Stanley D. Stearns, Houston, TX (US); H. Max Loy, Jr., Houston, TX (US)

(73) Assignee: Valco Instruments Company, L.P., Houston, TX (US)

( * ) Notice: Subject to any disclaimer, the term of this patent is extended or adjusted under 35 U.S.C. 154(b) by 226 days.

(21) Appl. No.: 15/298,822

(22) Filed: Oct. 20, 2016

(65) Prior Publication Data

US 2017/0254452 A1    Sep. 7, 2017

Related U.S. Application Data

(60) Provisional application No. 62/303,757, filed on Mar. 4, 2016.

(51) Int. Cl.
*F16L 19/02* (2006.01)
*G01N 30/60* (2006.01)

(52) U.S. Cl.
CPC ...... *F16L 19/0206* (2013.01); *G01N 30/6026* (2013.01)

(58) Field of Classification Search
CPC .......... G01N 30/6026; G01N 30/6034; G01N 30/6039; F16L 19/0206; F16L 19/0212
USPC ............................... 285/246, 342; 210/198.2
See application file for complete search history.

(56) References Cited

U.S. PATENT DOCUMENTS

| 5,570,447 | A | 10/1996 | Liu | |
|---|---|---|---|---|
| 9,091,693 | B2 | 7/2015 | Hochgraeber et al. | |
| 9,134,283 | B2 | 9/2015 | Hochgraeber et al. | |
| 2003/0146624 | A1 | 8/2003 | Gotoh | |
| 2009/0287200 | A1 | 11/2009 | Hanley et al. | |
| 2012/0024411 | A1* | 2/2012 | Hahn | G01N 30/6026 |
| 2014/0130580 | A1 | 5/2014 | McAdams | |
| 2014/0131997 | A1* | 5/2014 | Burger | G01N 30/6039 |
| 2015/0048015 | A1* | 2/2015 | Joudrey | G01N 30/6026 210/198.2 |

(Continued)

OTHER PUBLICATIONS

Blaine R. Copenheaver, Written Opinion of the International Searching Authority—PCT/US2017/012289, dated Feb. 24, 2017, 4 pages, United States Patent & Trademark Office as International Searching Authority, Alexandria, Virginia, USA.

(Continued)

*Primary Examiner* — David Bochna
*Assistant Examiner* — Zachary T Dragicevich
(74) *Attorney, Agent, or Firm* — Crain, Caton & James, P.C.; James E. Hudson, III

(57) ABSTRACT

A tubing and ferrule assembly for use in joining a clad tubing to a fitting. The ferrule is bound to the clad tubing, which includes a partial jacket of stainless steel, such that the inert core protrudes from, and has a common outer diameter with, the jacket. The ferrule is bound to the jacket slightly more distant than necessary for the inert core to contact a fitting. When the ferrule is retained in place, the inert core is compressed and provides a true zero dead volume connection between the clad tubing and the fitting. The relationship of the ferrule, the clad tubing, and the fitting limits the position of the clad tubing and therefore precludes damaging of the associated valve or component.

4 Claims, 3 Drawing Sheets

(56) References Cited

U.S. PATENT DOCUMENTS

2016/0116088 A1  4/2016  Graham et al.

OTHER PUBLICATIONS

Blaine R. Copenheaver, International Search Report—PCT/US2017/012289, dated Feb. 24, 2017, 2 pages, United States Patent & Trademark Office as Searching Authority, Alexandria, Virginia, USA.

Blaine R. Copenheaver, Notification of Transmittal of the International Search Report and the Written Opinion of the International Searching Authority, or the Declaration—PCT/US2017/012289, dated Feb. 24, 2017, 1 page, United States Patent & Trademark Office as Searching Authority, Alexandria, Virginia, USA.

Search History—PCT/US2017/012289, Feb. 24, 2017, 5 pages, United States Patent & Trademark Office as Searching Authority, Alexandria, Virginia, USA.

Harry C. Kim; International Preliminary Report on Patentability for PCT Application No. PCT/US17/12289; dated Feb. 7, 2018; 8 pages; USPTO as IPEA; Alexandria, Virginia.

* cited by examiner

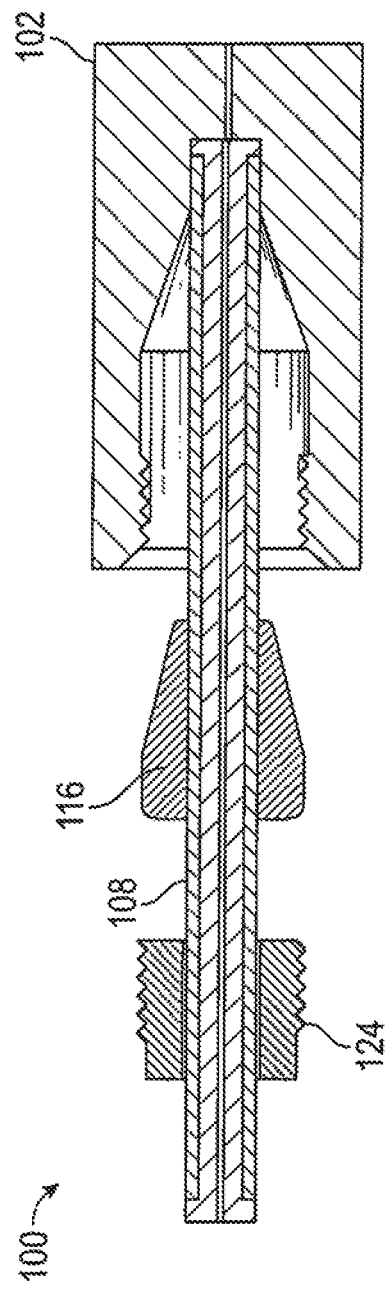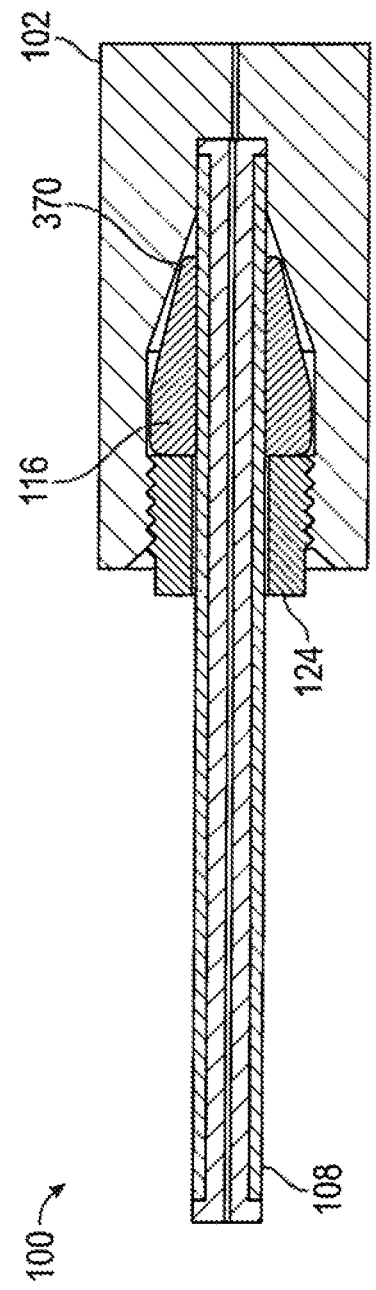

ZERO DEAD VOLUME FITTING ASSEMBLY

CROSS-REFERENCE TO RELATED APPLICATIONS

This application claims the benefit of U.S. Provisional Patent Application No. 62/303,757 entitled "Zero dead volume fitting assembly" filed on Mar. 4, 2016 in the United States Patent and Trademark Office and which is incorporated herein by reference.

STATEMENT REGARDING FEDERALLY SPONSORED RESEARCH OR DEVELOPMENT

Not Applicable.

FIELD

This disclosure pertains to fittings for use in systems designed for chemical analysis where zero dead volume is required.

BACKGROUND

It is necessary in analytical systems to have fittings that create leak-tight seals. In such analytical systems, it is also desirous to have fittings which are inert relative to the sample components, which provide a flow path without inducing turbulence or mixing, and which adds minimal volume to the system.

Fitting designs which best address the aspect of added volume allow the tube ends which pass through such fittings to butt directly to each other or have bores which match the tubing bore, leaving no dead or unswept volume. Such fittings are called zero dead volume fittings. In analytical testing apparati dead volume is to be avoided as it reduces efficiencies of the test equipment, including gas columns.

One of the most common types of such zero dead volume fittings is a compression fitting. A zero dead volume compression fitting consists of a fitting having a female fitting detail, tubing, a ferrule loosely riding on the tubing, and a male nut, also riding on the tubing. In operation the tubing is placed into the fining until the tubing end passes through the inner bore of the fitting, and seats correctly at the bottom of the fitting detail, the ferrule is then slid along the tubing until, it engages the mating walls of the fitting, and the nut is threadedly engaged so as to be retained in place and to deform the ferrule against the mating wall of the fitting detail, causing the ferrule to apply pressure to the tubing and force such tubing against the bottom of the fitting detail.

Basic problems with such system are inherent in the type and number of parts, namely the fitting, the ferrule, the tubing and nut. The fitting and ferrule need be sufficiently sized so that the ferrule can be deformed against the fitting to provide a seal, which often provides some volume at the interface of these components. The ferrule in these systems necessarily must be deformable to provide a seal, but the force necessary to do so may be exceeded and thus overdrive the tubing into the fitting and interfere with operation of the associated valve. This problem is acerbated in a multi-ported valve having a plurality of fitting bodies associated with it and the overtightening into one or more of the detail associated with a port. Moreover, these systems must sustain the associated high pressures, must not deform the associated fitting, and must not have any extraneous volume creating an undesirable mixing chamber.

SUMMARY

The present disclosure provides a high pressure tubing system including a tubing and a ferrule for use with a zero dead volume fitting as an ultra-high performance capillary tube connector. The zero dead volume fitting has a zero dead volume fitting detail sized to receive a clad tubing, a zero dead volume fitting detail pilot terminating at a zero dead volume fitting detail pilot bottom, and a zero dead volume fitting detail ferrule seat. The clad tubing has an inert polymer core and a stainless steel jacket, a core length, a jacketed core outer diameter, an unjacketed core outer diameter, a core first end, a core first end segment, a core second end, a core second end segment, a core intermediate segment and a core lumen therethrough. The inert polymer core is composed of a single monolithic piece and has a common diameter throughout. The core length extends from the core first end to the core second end. The core first end has a flat core first face at the core first end. The core intermediate segment is intermediate the core first end segment and the core second end segment. The stainless steel jacket has a jacket length, a jacket outer diameter, a jacket inner diameter, a jacket thickness and a jacket first end. The core length is greater than the jacket length. The stainless steel jacket is positioned about the core intermediate segment. The jacket thickness is half the difference between the jacket outer diameter and the jacket inner diameter. The jacket inner diameter is equivalent to the jacketed core outer diameter and the jacket outer diameter is equivalent to the unjacketed core outer diameter. The stainless steel jacket is positioned about the core intermediate segment. The ferrule initially is slidably positioned about the clad tubing to the stainless steel jacket, and has a first end and a ferrule second end and has a wedge-shaped face sized to contact the zero dead volume fitting detail ferrule seat proximate the ferrule first end at a point of contact. The ferrule is ultimately retained in position around the clad tubing such that the ferrule first end is at a tubing pilot length from the core first end of the inert polymer core.

BRIEF DESCRIPTION OF THE DRAWINGS

So that the manner in which the described features, advantages and objects of the disclosure, as well as others which will become apparent, are attained and can be understood in detail, more particular description of the disclosure briefly summarized above may be had by reference to the embodiments thereof that are illustrated in the drawings, which drawings form a part of this specification. It is to be noted, however, that the appended drawings illustrate only a typical preferred embodiment of the disclosure and are therefore not to be considered limiting of its scope as the disclosure may admit to other equally effective embodiments.

In the drawings:

FIG. 2 is a cross sectional view of the assembly in connection with a fitting at initial insertion.

FIG. 3 is a cross sectional view of the assembly in connection with a fitting at thin point of contact of the ferrule and retaining member with the fitting.

DESCRIPTION OF THE PREFERRED EMBODIMENT

Figure 1:
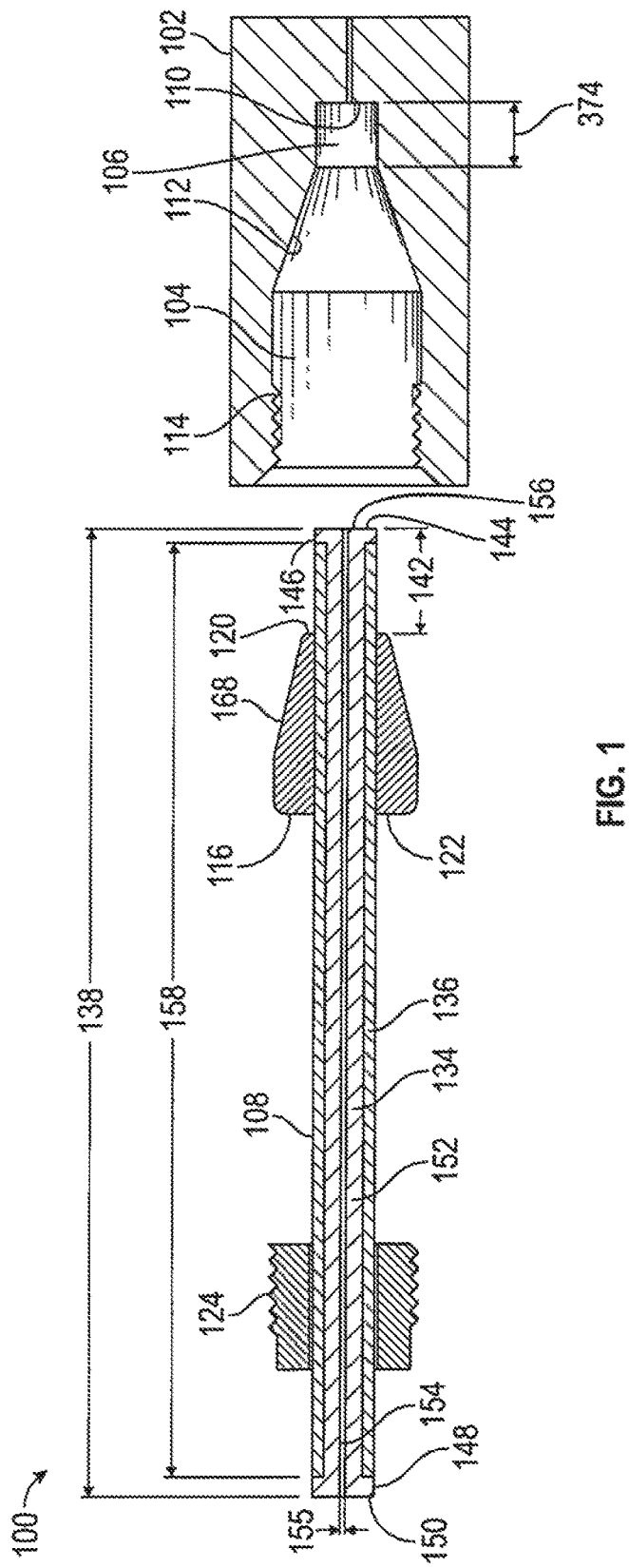
FIG. 1 is a cross sectional view of the assembly in connection with a fitting prior to insertion.

The zero dead volume fitting assembly is provided in the present disclosure. Referring to FIG. 1, the high pressure tubing system 100, a capillary tubing connector system, includes a ferrule 116 and a clad tubing 108, to be used in connection with a retaining member 124, which may be a nut or other threaded body. The high pressure capillary tubing connector system 100 provides a zero dead volume connection particularly beneficial for chromatography. The high pressure capillary tubing connector system 100 provides a zero dead volume connection to a zero dead volume fitting 102 which has a zero dead volume fitting detail 104, and which includes a zero dead volume fitting detail pilot 106 sized to receive the clad tubing 108. The zero dead volume fitting detail pilot 106 terminates at a zero dead volume fitting detail pilot bottom 110. The zero dead volume fitting detail 104 also has a zero dead volume fitting detail ferrule seat 112 and a zero dead volume fitting retention section 114, such as female threads, therein.

Referring to FIG. 1, the present disclosure provides the stainless steel jacket 136 about the inert polymer core 134, which stainless steel jacket 136 prevents deformation of the inert polymer core 134 in response to high pressure, but which terminates short of the polymer end, resulting in a jacketed core intermediate segment 152, a core first end segment 146, and a core second end segment 148. The stainless steel jacket 136, which is positioned about substantially all of the inert polymer core 134, ensures that the core first end segment 146 and the core second end segment 148 extend beyond the stainless steel jacket 136 so as to provide a compressible sealing surface composed solely of the inert polymer core 134.

To accommodate higher pressures and to provide a surface for the ferrule 116 to bite into, the clad tubing 108 includes an inert polymer core 134 and a stainless steel jacket 136, which is positioned about substantially all of the inert polymer core 134 and is clad thereabout. The inert polymer core 134 is adapted to convey a sample of liquid or gas, potentially at a high pressure, without contaminating the sample, by construction from an inert material. The inert polymer core 134 is also selected from an inert material which can be compressed to provide a seal against a mating flat surface. The mating flat surface may be composed of steel. The inert polymer core 134 may be of a flexible inert materials PEEK (Poly Ether Ether Ketone), PTFE (PolyTetraFluoroEthylene), ETFE (ethylene-tetrafluoroethylene), FEP (Flouridated Ethylene-Propylene), PFA (Perfluoroalkoxyethylene), and nylon. Such an inert polymer core 134, while providing an inert surface for transportation of a sample, is known to be unable to sustain the pressure associated with such chromatographic uses.

Referring to FIG. 1, the high pressure capillary tubing connector system 100 includes a ferrule 116, which encircles, and may be ultimately fixed in position about, the clad tubing 108. The ferrule 116 has a ferrule first end 120, sometimes referred to as a nose, and a ferrule second end 122, sometimes referred to as a heel, and has a ferrule wedge-shaped conical section 168 proximate the ferrule first end 120. The clad tubing 108 has a tubing pilot length 142 greater than the zero dead volume fitting detail pilot length 374. The tubing pilot length 142 is more than the sum of the zero dead volume fitting detail pilot length 374 illustrated in FIG. 1 and the core first end segment length 468 illustrated in FIG. 4. Thus, the tubing pilot length 142 is slightly greater than a zero dead volume fitting detail pilot length 374 of the zero dead volume fitting detail 104, and generally becomes closer to the zero dead volume fitting detail pilot length 374 when the core first end segment 146 is compressed by the driving force of the ferrule 116 to provide a seal at the core first end flat face 156 against the zero dead volume fitting pilot bottom 110.

Figure 4:
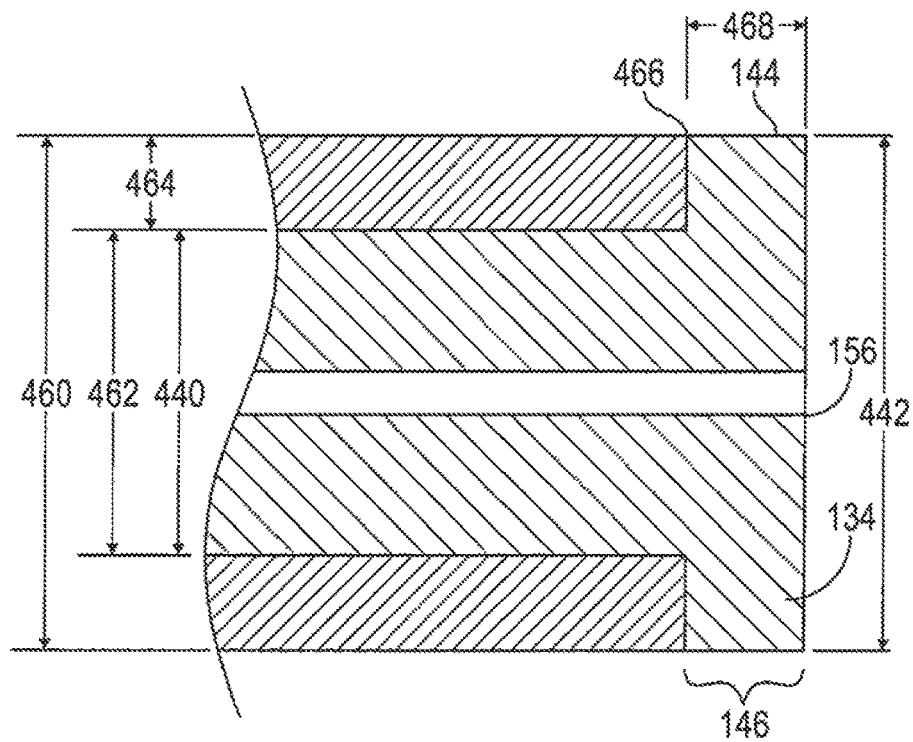
FIG. 4 is a cross sectional view of the first end of the clad tubing.
Figure 5:
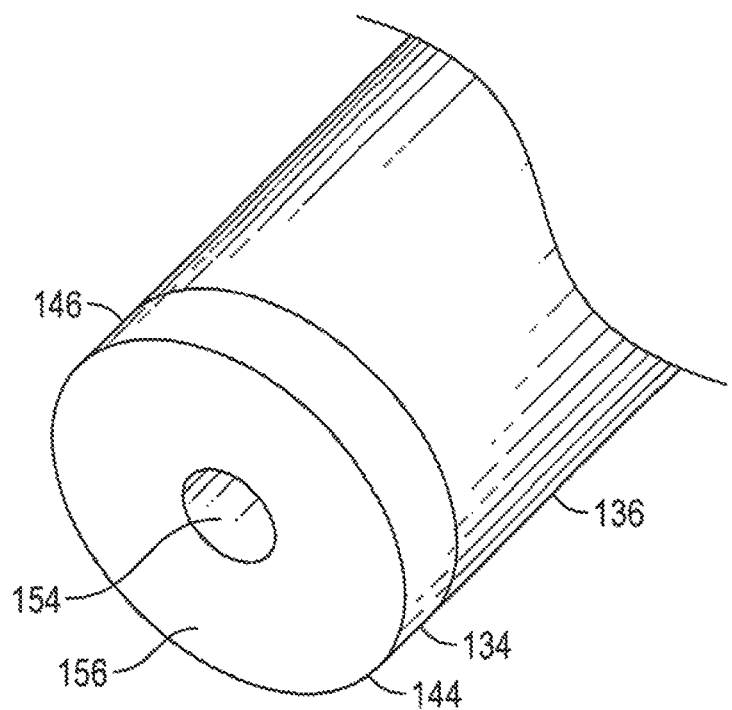
FIG. 5 is an isometric view of the first end of the clad tubing.

Referring to FIGS. 1, 4 and 5, the inert polymer core 134 has a core length 138, a jacketed core outer diameter 440, an unjacketed core outer diameter 442, a core first end 144, a core first end segment 146, a core second end 150, a core second end segment 148, a core intermediate segment 152, and a core lumen 154 therethrough. The core length 138 extends from the core first end 144 to the core second end 150. The core lumen 154 has a fixed, constant, small core lumen diameter 155 throughout, which may be less than 0.03 inches. This fixed and constant core lumen diameter 155, together with the core first end flat face 156 at the core first end 144 ensures a fixed cross sectional area throughout and therefore avoids any potential "mixing chamber" within the fitting.

Referring to FIGS. 1 and 4, the stainless steel jacket 136 has a jacket length 158, a jacket outer diameter 460 and a jacket inner diameter 462, a jacket thickness 464, and a jacket first end 466. The core length 138 is greater than the jacket length 158, resulting in the core first end segment 146 and the core second end segment 148 extending beyond the stainless steel jacket 136. The stainless steel jacket 136 is therefore positioned about the core intermediate segment 152. The stainless steel jacket 136 may have a thickness half the difference between the jacket outer diameter 460 and the jacket inner diameter 462.

Referring to FIGS. 1 and 4, because the stainless steel jacket 136 surrounds the inert polymer core 134 and is positioned about the core intermediate segment 152, the jacket inner diameter 462 is equivalent to the jacketed core outer diameter 440. Because the jacket length 158 is less than the core length 138, the inert polymer core 134 extends sufficiently beyond the stainless steel jacket 136, to provide a core first end segment 146 at the core first end 144 and the core second end segment 148 at the core second 150. The core intermediate segment 152 is intermediate the core first end segment 146 and the core second end segment 148. Additionally, the jacket outer diameter 460 is equivalent to the unjacketed core outer diameter 442. This tight encirclement of the inert polymer core 134 by the stainless steel jacket 136 permits the use of a chemically inert tubing in contact with the fluid flowing therethough and permits the pressure in the inert polymer core 134 to exceed the capabilities of the inert polymer core 134. The potential for the inert polymer core 134 to fail under pressure is eliminated by the encirclement of the core first end segment 146 within the zero dead volume fitting detail pilot 106 and the jacketing of the inert polymer core 134 by the stainless steel jacket 136, which resist any high pressure deformation or failure.

Referring to FIGS. 1, 4 and 5, the fixed and constant core lumen diameter 155 of the core lumen 154 and the core first end flat face 156, together provide a primary seal surface across the end of the clad tubing 108. Unlike the prior art, which may provide a hardened ring about the perimeter of the tubing, the provision of the core first end flat face 156 at the core first end 144 under compression precludes the creation of a mixing chamber intermediate the end of the core lumen 154 and the zero dead volume fitting detail bottom 110. In operation, this provides the primary seal upon compression of the core first end segment 146. This compression is provided by force applied from a ferrule 116 maintained in the zero dead volume fitting 102 at a fixed and beneficial location which precludes unnecessary force being applied to the zero dead volume fitting detail bottom 110 and thus overtightening.

Referring to FIG. 1, the ferrule 116 is fixed or bound to the clad tubing 108 by cutting into the stainless steel jacket 136 with the ferrule first end 120, with the ferrule first end 120 is positioned at a tubing pilot length 142. By fixing the ferrule 116 to the clad tubing 108 at this point, the extent of compression of the core first end segment 146 is fixed and the force applied to the core first end flat face 156 of the clad tubing 108 is limited so as to neverapply such force as to damage the associated valve.

Referring to FIG. 2, the assembled ferrule 116 and retention member 124 may alternatively initially be loosely positioned on the clad tubing 108. This initially freely-moving assembly may be desirable to address any potential tolerance issues of the specific zero dead volume fitting 102. As can be appreciated, a zero dead volume fitting detail pilot length 374 may vary from zero dead volume fitting 102 to zero dead volume fitting 102. Thus, it may be desirable to cause the ferrule 116 to become fixed to the clad tubing 108 in connection with a particular zero dead volume fitting 102. The clad tubing 108 is positioned into the zero dead volume fitting detail 104 of the zero dead volume fitting 102, and particularly into the zero dead volume fitting detail pilot 106, until the core first end 144 contacts the zero dead volume fitting detail pilot bottom 110 at the core first end flat face 156.

Referring to FIGS. 1 and 3, the loose ferrule 116 is driven into the zero dead volume fitting detail 104 and maintained in position by the retention member 124, which engages the retention section 114 of the zero dead volume fitting 102. The zero dead volume fitting detail 104 includes a zero dead volume fitting detail pilot 106 sized to receive and fit about the clad tubing 108 at its core first end 144 and particularly to receive the core first end segment 146, thus constraining the inert polymer core 134 against deformation from internal pressures. Some portion of the stainless steel jacket 136 preferably also is received in the zero dead volume fitting detail pilot 106. The ferrule wedge-shaped conical section 168 of the ferrule 116 contacts the zero dead volume fitting detail ferrule seat 112 at the point of contact 370. Any coupling means may be used in addition to the threaded assembly for the retaining member 124 and the retention section 114, such as a cam and groove connector, an express coupling, a Guillemin symmetrical clutch coupling, a Mulconroy IX fitting, or any other fitting, particularly those adapted to high pressure situations. The retaining member 124 may have wings, such as associated with a wingnut, or may have an outer surface which presents an irregular or non-circular surface, such as a hex head, or a head providing a keyed surface, such as an extending body, about which a mating collar can fit and provide leverage for rotation.

Referring to FIGS. 1 and 3, further tightening of the retention member 124 first causes the retention member 124 to proceed further into the zero dead volume fitting 102 and to apply force against the ferrule 116, causing it to be slightly deformed and, because of the narrowing of the zero dead volume fitting detail ferrule seat 112, to cause the ferrule 116, at the ferrule first end 120, to be constricted about its circumference and to bite into the clad tubing 108. Once the ferrule 116 bites into the clad tubing 108, the ferrule 116 is bound to, or made up with, the clad tubing 108. The ferrule 116 having bitten into the stainless steel jacket 136 of the clad tubing 108, the ferrule first end 120 is fixed a tubing pilot length 142 from the zero dead volume fitting detail pilot bottom 110, as illustrated in FIGS. 1 and 3. Thereafter the ferrule 116 and the clad tubing 108 are not readily separated or the position of the ferrule 116 on the clad tubing 108 to be altered, as described in connection with FIG. 1.

Referring to FIGS. 1 and 3, beneficially, once the ferrule 116 has bitten into the clad tubing 108, in the event they are removed from the zero dead volume fitting 102, the two can be replaced in the zero dead volume fitting 102 and lightly tightened into position, such as by fingertightening or by use of a small tool. Now, the retaining member 124 can only be tightened into the zero dead volume fitting retention section 114 until the ferrule 116 contacts the zero dead volume detail fitting seat 112, after which further tightening provides no advance of the ferrule 116 moreover, the ferrule 116 acts as stop to prevent unnecessary force being applied to the zero dead volume fitting detail bottom 110.

With the ferrule 116 bound to the clad tubing 108 tightening of the retention member 124 causes the clad tubing 108 to be driven forward toward the zero dead volume fitting detail pilot bottom 110 and to compress the core first end segment 146 against the zero dead volume fitting detail pilot bottom 110 until the ferrule wedge-shaped conical section 168 of the ferrule 116 contacts the zero dead volume fitting detail ferrule seat 112 at the point of contact 370 and can be driven no further forward. Thus, tightening the retaining member 124 in the zero dead volume fitting 102 at the zero dead volume fitting retention section 114 applies sufficient force for the core first end segment 146 to be compressed against the zero dead volume fitting detail pilot bottom 110 and for the core first end flat face 156 of the core first end 144 to contact so as to provide a sufficient primary seal. Additionally, this provides sufficient force for the ferrule 116 to be pressed tightly against the zero dead volume fitting detail ferrule seat 112 to provide a secondary seal and prevent unnecessary force being applied primary seal.

Referring to FIGS. 1, 4 and 5, unlike the prior art, because the clad tubing 108 provides a core lumen 154 of fixed, constant, small core lumen diameter 155, no mixing chamber is created within the zero dead volume fitting detail 104. Moreover, because the ferrule 116 has bitten into the clad tubing 108, and because the clad tubing 108 provides compressible core first end segment the force which may thereafter be applied by the core first end flat face 156 at the core first end 144 against the zero dead volume fitting detail pilot bottom 110 is limited and made insufficient to distort any chromatographic component with which the zero dead volume fitting 102 is associated, particular a valve. That distortion was known to cause separation of the rotor and stator in a valve, causing undesirable leakage and loss of pressurization. Moreover, the ferrule 116, which cannot be fingertightened beyond the point of contact 370, serves as a stop to prevent distortion or destruction of associated component, often a valve. Where such as stop is not provided, overdriving of tubing is known to distort or permanently damage the associated fitting, resulting in at least degraded data.

Referring again to FIGS. 1 and 3, as the ferrule wedge-shaped conical section 168 of the ferrule 116 contacts the zero dead fitting 102 at a point of contact 370 a secondary seal is provided. Because the force to tighten the ferrule 116 and to bite into the clad tubing 108 may be greater than necessary to maintain contact with the zero dead volume 102, and thus provide a seal, the retaining member 124 may be loosened while maintaining contact with the point of contact 370. As can be appreciated, the retaining member 124 may require only minimal force to sufficient engage the zero dead volume fitting 102, such as by fingertightening. This may be particularly beneficial in chromatography uses, where the zero dead volume fitting 102 may be one of several ports associated with a single, small valve, each of which would have a clad tubing emanating therefrom about the valve's central axis.

It will be understood that while a preferred embodiment of the disclosure has been shown and described, the disclosure is not limited thereto. Many modifications may be ad e and will become apparent to those skilled in the art.

The invention claimed is:

1. A high pressure capillary tubing connector system (100) for use with a zero dead volume fitting (102),
    having a zero dead volume fitting detail (104),
        the zero dead volume fitting detail (104) having a zero dead volume fitting detail pilot (106) sized to receive and fit about a clad tubing (108) along the entirety of a zero dead volume fitting detail pilot length (374),
        the zero dead volume fitting detail pilot (106) terminating at a zero dead volume fitting detail pilot bottom (110),
        the zero dead volume fitting detail (104) having a zero dead volume fitting detail ferrule seat (112),
    the high pressure capillary tubing connector system (100) comprising:
    the clad tubing (108),
        the clad tubing (108) having an inert polymer core (134) and a stainless steel jacket (136), the inert polymer core (134) having a core length (138), a jacketed core outer diameter (440), an unjacketed core outer diameter (442), a core first end (144) a core first end segment (146), a core second end (150), a core second end segment (148), a core intermediate segment (152) and a core lumen (154) therethrough, the core lumen (154) having a core lumen diameter (155) of constant diameter throughout,
            the core length (138) extending from the core first end (144) to the core second end (150),
            the core first end (144) having a core first end flat face (156) at the core first end (144),
            the core intermediate segment (152) being intermediate the core first end segment (146) and the core second end segment (148),
            the core first end segment (146) having a core first end segment length (468)
        the stainless steel jacket (136) having a jacket length (158), a constant jacket outer diameter (460) along the jacket length (158), a jacket inner diameter (462), a jacket thickness (464) along the jacket length (158) and a jacket first end (466),
            the core length being greater than the jacket length (158),
            the stainless steel jacket (136) positioned about the core intermediate segment (152),
            the jacket thickness (464) being half the difference between the jacket outer diameter (460) and the jacket inner diameter (462),
            the jacket inner diameter (462) being equivalent to the jacketed core outer diameter (440),
            the jacket outer diameter (460) being equivalent to the unjacketed core outer diameter (442); and
    a ferrule (116),
        the ferrule (116) bound to the stainless steel jacket (136) of the clad tubing (108),
        the ferrule (116) having a ferrule first end (120),
        the ferrule (116) having a ferrule second end (122),
        the ferrule (116) having a ferrule wedge-shaped conical section (168) sized to contact the zero dead volume fitting detail ferrule seat (112) proximate the ferrule first end (120) at a point of contact (370),
        the ferrule (116) bound to the stainless steel jacket (136) a tubing pilot length (142) from the core first end (144) of the inert polymer core (134),
            the tubing pilot length (142) greater than the zero dead volume fitting detail pilot length (374) but more than the sum of the zero dead volume fitting detail pilot length (374) and the core first end segment length (468).

2. The high pressure tubing system of claim 1, further comprising:
    a retaining member (124),
        the retaining member (124) adapted to removably apply force against the ferrule second end (122),
        the retaining member (124) adapted to maintain position relative to the zero dead volume fitting (102) while maintaining the ferrule first end (120) at the point of contact (370).

3. The high pressure tubing system of claim 2, wherein the retaining member (124) is a nut having an external threaded surface and wherein the zero dead volume fitting detail (104) includes an internally threaded surface.

4. A high pressure capillary tubing connector system (100) for use with a zero dead volume fitting (102),
    having a zero dead volume fitting detail (104),
        the zero dead volume fitting detail (104) having a zero dead volume fitting detail pilot (106) sized to receive and fit about a clad tubing (108) along the entirety of a zero dead volume fitting detail pilot length (374),
        the zero dead volume fitting detail pilot (106) terminating at a zero dead volume fitting detail pilot bottom (110),
        the zero dead volume fitting detail (104) having a zero dead volume fitting detail ferrule seat (112),
    the high pressure capillary tubing connector system (100) comprising:
    the clad tubing (108),
        the clad tubing (108) having an inert polymer core (134) and a stainless steel jacket (136), the inert polymer core (134) having a core length (138), a jacketed core outer diameter (440), an unjacketed core outer diameter (442), a core first end (144) a core first end segment (146), a core second end (150), a core second end segment (148), a core intermediate segment (152) and a core lumen (154) therethrough, the core lumen (154) having a core lumen diameter (155) of constant diameter throughout,
            the core length (138) extending from the core first end (144) to the core second end (150),
            the core first end (144) having a core first end flat face (156) at the core first end (144),
            the core intermediate segment (152) being intermediate the core first end segment (146) and the core second end segment (148),
        the stainless steel jacket (136) having a jacket length (158), a constant jacket outer diameter (460) along the jacket length (158), a jacket inner diameter (462), a jacket thickness (464) along the jacket length (158) and a jacket first end (466),
            the core length being greater than the jacket length (158), the stainless steel jacket (136) positioned about the core intermediate segment (152), the jacket thickness (464) being half the difference between the jacket outer diameter (460) and the jacket inner diameter (462), the jacket inner diameter (462) being equivalent to the jacketed core outer diameter (440), the jacket outer diameter (460) being equivalent to the unjacketed core outer diameter (442); and a ferrule (116), the ferrule (116) encircling to the stainless steel jacket (136) of the clad tubing (108), the ferrule (116) having a ferrule first end (120), the ferrule (116) having a ferrule second end (122), the ferrule (116) having a ferrule wedge-shaped conical section (168) sized to contact the zero dead volume fitting detail ferrule seat (112) proximate the ferrule first end (120) at a point of contact (370).

\* \* \* \* \*